United States Patent [19]
Lavallee et al.

[11] 4,013,414
[45] Mar. 22, 1977

[54] INDICATOR DYE

[75] Inventors: Francois A. Lavallee, Willoughby Hills, Ohio; Donald G. LeGrand, Burnt Hills; George L. Gaines, Jr., Scotia, both of N.Y.

[73] Assignee: General Electric Company, Schenectady, N.Y.

[22] Filed: May 5, 1975

[21] Appl. No.: 574,725

[52] U.S. Cl. .............................. 23/230 R; 23/230 M
[51] Int. Cl.² ................ G01N 31/00; G01N 31/22
[58] Field of Search ................................. 23/230 R

[56] References Cited
UNITED STATES PATENTS

| | | | |
|---|---|---|---|
| 3,490,874 | 1/1970 | Ando et al. | 23/230 R |
| 3,576,815 | 4/1971 | Doyle | 23/230 R |
| 3,706,537 | 12/1972 | Becher et al. | 23/230 R |

OTHER PUBLICATIONS

Brooker, L.G.S.; Keyes, G. W. & Heseltine, D. W.; Color and Constitution XI Anhydronium Bases of P-hydroxystyryl Dyes as Solvent Polarity Indicators; Journal of the American Chemical Society, vol. 73, pp. 5350–5356; 1951.

Hawley, Gessner G.; The Condensed Chemical Dictionary 8th ed.; pp. 249–250; 1971.

Primary Examiner—Norman Yudkoff
Assistant Examiner—Dale Lovercheck
Attorney, Agent, or Firm—John F. McDevitt; Lawrence R. Kempton; Frank L. Neuhauser

[57] ABSTRACT

A novel class of soluble organic nitrogen compounds which produces various colors when dissolved in organic liquid solvents. These dyes produce a color from blue to red if the organic liquid medium has a neutral or basic pH which reversibly changes to yellow if the liquid medium has an acid pH. The color variation can also serve as an indication of solvent polarity.

8 Claims, 1 Drawing Figure

OPTICAL ABSORPTION MEASUREMENTS

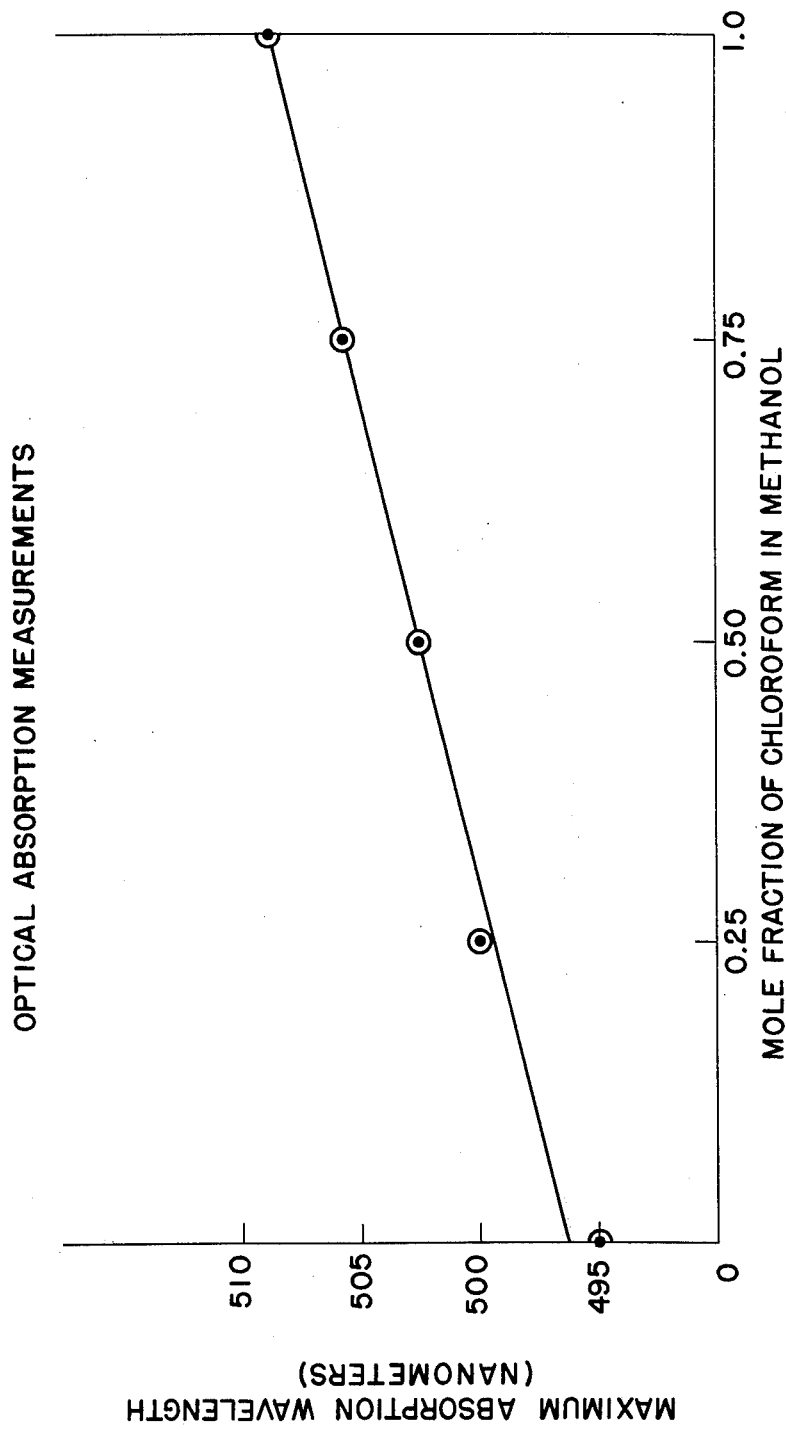

INDICATOR DYE

BACKGROUND OF THE INVENTION

The present invention relates to a novel class of soluble organic nitrogen compounds which produce a highly visible color when dissolved in organic liquid solvents. An original color ranging from blue to red is produced in the organic solution depending upon the relative polarity of the particular organic liquid solvent and which changes to a yellow color if the particular liquid organic medium becomes acidified. The original color can be reproduced in said organic liquid medium upon conversion to a neutral or basic pH by such conventional means as adding a soluble base or bubbling gaseous ammonia through the medium.

Various acid-base indicator dyes are known to produce a color change in both aqueous and non-aqueous liquid medium upon acidification. Cresol Red is a well known organic dye which changes color when acidification occurs in a particular solution. A more recently discovered organic nitrogen dye exhibiting different colors in aqueous and pyridine solutions has been reported by Brooker, Keyes & Heseltine in Journal of the American Chemical Society, Volume 73, page 5350 (1951). The particular dye is reported to have the chemical formula

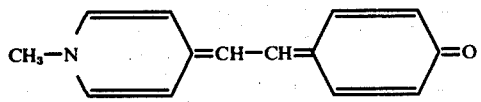

and the color shift is attributed to different resonance forms of the dye molecule.

SUMMARY OF THE INVENTION

Basically, the present invention comprises a soluble organic nitrogen compound having a general formula

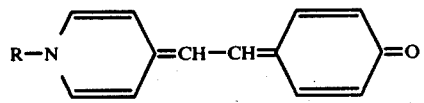

wherein R is an aliphatic hydrocarbon radical having approximately 12 to 20 carbon atoms. This class of organic compounds can be regarded as a long-chain aliphatic derivative of a merocyanine dye which is insoluble in water but soluble in a wide range of organic solvents including both polar and non-polar liquids. The present dyes exhibit colors ranging from blue and blue-purple to orange and red as the polarity of the organic solvent increases. The color produced upon acidification of the organic solvent medium is usually yellow when a protonic acid such as HCl provides the acid condition. The present dye materials are in the form of crystalline solids which can be dissolved in various organic solvents at concentrations as low as $10^{-6}$ molar to permit visible detection of an acid condition.

The present dyes have further utility as indicators of solvent polarity and in the study of chemical reactions taking place in organic solvents. For example, the concentration of a particular organic solvent in an organic solvent mixture can be measured from the optical absorption characteristics of the particular mixture. A direct relationship has been found to exist between the maximum absorption wavelength measured for a particular organic solvent mixture and the molar concentration of solvents in said mixture.

DESCRIPTION OF THE DRAWING

The drawing is a graph depicting the wavelength of maximum absorption in various mixtures of chloroform and methanol containing a preferred dye compound of the present invention.

DESCRIPTION OF THE PREFERRED EMBODIMENTS

Applicants have discovered that particular organic nitrogen compounds having the above defined general structural formula provide efficient indicia means when dissolved in various liquid media employing organic solvents. A useful result which can be obtained with such use of the present dyes is for qualitative and quantitative detection of acidity or acid buildup in non-aqueous solvents. For example, the presence of acids in organic solvents can lead to corrosion of equipment or contamination of products. Typical applications in which these dyes could be used to detect unwanted acid buildup or acidity include metal degreasing systems, dry cleaning systems (especially those using chlorinated hydrocarbon solvents), dielectric fluids petroleum oils, unsaturated fats, and oils, etc. This can be especially important with respect to chlorinated solvents which are known to decompose when exposed to light and form acid products such as might occur in chloroform. The present dyes may also prove useful as an aerosol applied developing agent in thin layer chromatography of organic acids, amino-acid hydrochlorides, and still other product applications.

To illustrate preparation of the dye containing 16 carbon atoms in the aliphatic hydrocarbon chain a halogen derivative of the hydrocarbon is reacted with 4-picoline in an organic liquid solution to form a first condensation product. Said first condensation product is further reacted with p-hydroxybenzaldehyde to form a second condensation product which can be prepared in the same liquid reaction mixture by addition of catalytic amounts of piperidine. The dye product is obtained by treating the liquid reaction mixture with gaseous ammonia and/or sodium hydroxide to remove unreacted starting materials as well as halide ion from the second condensation product. Evaporation of organic solvent from said liquid reaction mixture allows the final product to be separated physically as a solid precipitate which can thereafter be collected by filtration for final purification in conventional fashion.

Various methods are contemplated for use of the present dye materials as colorometric indicia means in liquid media employing one or more organic solvents. In a preferred embodiment, the acid condition of such liquid media can be detected either by direct visual observation or with known colorometric instruments measuring the color change. In a different preferred method, the present dye materials are employed to measure the concentration of a particular solvent in a solvent mixture. A known optical absorption instrument such as a Cary spectrophotometer can be used to measure the maximum absorbance in said mixed organic solvents having the dye material dissolved therein. The accompanying drawing depicts optical absorption measurements made upon various concentrations of chloroform in methanol. Both of the foregoing methods are further deemed useful in the study of chemical reactions taking place in organic solvents. Accordingly, the following specific examples are provided to more clearly explain these various utilizations of the present dye materials.

EXAMPLE 1

Visual color changes produced by an acid condition in various organic solvents were observed utilizing the preferred dye material wherein the aliphatic hydrocarbon chain has 16 carbon atoms. The concentration of HCl in these solvents along with the concentration of dissolved dye material and the color changes produced are listed in the table below.

| Solvent | Initial Color | Final Color | Molar Acid Concentration at Color Change |
|---|---|---|---|
| Tetrachloroethylene | Blue | Yellow | $19 \times 10^{-5}M$ |
| Dichloroethane | Blue | Yellow | $5 \times 10^{-5}M$ |
| Chloroform | Purple | Yellow | $1.8 \times 10^{-5}M$ |

In the above tests the dye material was added to the solvent at concentrations less than $10^{-5}$ molar dye concentration in the particular solvents above listed.

EXAMPLE 2

An exemplary method which can be used to identify the concentration of a particular organic solvent in mixed organic solvents utilizes the same dye material employed in the preceding example. The dye was dissolved at an equal concentration in various mixtures of chloroform in methanol. Enough of the $2.3 \times 10^{-3}$ molar concentration solution of dye material in methanol was added to said solvent mixtures to yield equal concentrations of the dye material in each solution. The solvent mixtures were prepared by measuring out volumes of methanol and chloroform which after combination provided concentrations of 0, 0.25, 0.50, 0.75 and 1.0 mol fraction of chloroform in methanol. The maximum absorption wavelengths measured by a Cary spectrophotometer for the dye containing solvent mixtures are reported in the accompanying graph. It is apparent from these measurements that a nearly linear relationship exists between the optical absorption and the concentration of chloroform in this solvent mixture. The same type relationship is believed to occur in solvent mixtures employing two or more short chain aliphatic hydrocarbon solvents having up to 6 carbon atoms although the optical absorption for such mixtures has been found to further depend, at least in part, upon the polarity of the particular solvents employed.

It will be apparent from the foregoing description that novel dye materials have been discovered which provide sensitive indicator means by undergoing color change in organic solvents. It is not intended to limit the present invention to the preferred embodiments above described, however, since it will be apparent that still other methods of employing the present dye materials can prove useful. For example, the preferred dye material can be dissolved in organic solvents to provide a spot reagent for detecting the presence of acid compounds in solid form. It is intended, therefore, to limit the present invention only to the scope of the following claims.

We claim:

1. A method of identifying the acid condition of a liquid medium employing an organic solvent which comprises dissolving in said liquid medium a quantity of a soluble dye having the general formula

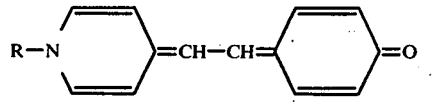

wherein R is an aliphatic hydrocarbon radical having approximately 12 to 20 carbon atoms so that color changes shift to longer wavelengths with increasing polarity of solvent and observing the color produced thereby.

2. A method as in claim 1 wherein the liquid medium includes an aromatic solvent.

3. A method as in claim 1 wherein the liquid medium includes an organic polar solvent.

4. A method as in claim 3 wherein the liquid medium includes a short chain aliphatic hydrocarbon solvent having from 1 to 6 carbon atoms.

5. A method of identifying the concentration of a particular organic solvent in a liquid medium employing mixed organic solvents which comprises dissolving in said liquid medium a quantity of a soluble dye having the general formula

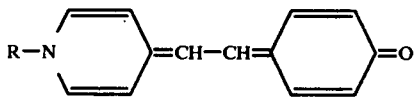

wherein R is an aliphatic hydrocarbon radical having approximately 12 to 20 carbon atoms so that color changes shift to longer wavelengths with increasing polarity of solvent and measuring the wavelength of maximum optical absorption of visible light in said liquid medium.

6. A method as in claim 5 wherein the liquid medium includes an aromatic solvent.

7. A method as in claim 5 wherein the liquid medium includes an organic polar solvent.

8. A method as in claim 10 wherein the liquid medium includes a short chain aliphatic hydrocarbon solvent having from 1 to 6 carbon atoms.

* * * * *